US008376966B2

(12) United States Patent
Miura

(10) Patent No.: US 8,376,966 B2
(45) Date of Patent: Feb. 19, 2013

(54) EVALUATING SYSTEM OF MASTICATORY EFFICIENCY AND ARTIFICIAL FOOD MATERIAL

(75) Inventor: Fujio Miura, Nerima-ku (JP)

(73) Assignee: Examastica Co., Tokyo (JP)

( * ) Notice: Subject to any disclaimer, the term of this patent is extended or adjusted under 35 U.S.C. 154(b) by 211 days.

(21) Appl. No.: 12/375,718

(22) PCT Filed: Aug. 14, 2007

(86) PCT No.: PCT/JP2007/065840
§ 371 (c)(1),
(2), (4) Date: Jan. 30, 2009

(87) PCT Pub. No.: WO2008/020588
PCT Pub. Date: Feb. 21, 2008

(65) Prior Publication Data
US 2009/0312671 A1    Dec. 17, 2009

(30) Foreign Application Priority Data
Aug. 15, 2006  (JP) ................................. 2006-221460

(51) Int. Cl.
A61B 5/103 (2006.01)
A61B 5/117 (2006.01)
G01N 31/00 (2006.01)
G01N 33/00 (2006.01)
A61C 19/04 (2006.01)
A61C 9/00 (2006.01)

(52) U.S. Cl. ..................... 600/590; 600/587; 252/408.1; 433/69; 433/71

(58) Field of Classification Search ................ 600/587, 600/590; 252/408.1; 433/69, 71
See application file for complete search history.

(56) References Cited

U.S. PATENT DOCUMENTS

| 5,410,028 | A * | 4/1995 | Asami et al. ....................... 536/2 |
| 5,698,181 | A | 12/1997 | Luo |
| 2005/0220713 | A1* | 10/2005 | Ohyama et al. ................ 424/9.6 |
| 2008/0107770 | A1 | 5/2008 | Wittorff et al. |
| 2008/0121023 | A1 | 5/2008 | Nokubi et al. |
| 2009/0053671 | A1* | 2/2009 | Abiru et al. ...................... 433/69 |

FOREIGN PATENT DOCUMENTS

| JP | 4-304848 A | 10/1992 |
| JP | 3001044 U | 8/1994 |
| JP | 2900947 B2 | 6/1999 |
| WO | WO 2006/046377 A1 | 5/2006 |
| WO | WO 2008111411 A1 * | 9/2008 |

OTHER PUBLICATIONS

Julien K.C. et al. "Normal Masticatory Performance in Young Adults and Children." Archs Oral Biology. vol. 41. p. 69-75. 1996.*
Akeel R.F. "Masticatory Efficiency, a Literature Review." The Saudi Dental Journal. vol. 4. May 1992.*
Sata, H et al. "A New and Simple Method for Evaluation Masticatory Funciton Using Newly Developed Atificial Test Food." Journal of Oral Rehabilitation. vol. 30. p. 68-73. 2003.*
Rivaldo et al. "Protocol for Production of a Chewable Material for Masticatory Function Tests (Optocal—Brazilian version)." Braz Oral Res. 2008.*
Duarte Gaviao, Maria Beatriz DDS, MS, PhD et al. "Masticatory Efficiency in Children with Primary Dentition." American Academy of Pediactric Dentistry. Pediactric Dentistry 23:6. 2001.*
Hirano Kei et al., "A Study on Measurement of Masticatory Ability Using a Color-changeable Chewing Gum with a New Coloring Reaction," J Jpn Prosthodont Soc, 2002, pp. 103-109, vol. 46.
International Search Report (PCT/ISA/210) dated Oct. 25, 2007.

* cited by examiner

Primary Examiner — Jeffrey G Hoekstra
Assistant Examiner — Adam Eiseman
(74) Attorney, Agent, or Firm — Buchanan Ingersoll & Rooney PC

(57) ABSTRACT

The present invention provides a evaluating system of masticatory efficiency comprising a first step of allowing a human subject to masticate an artificial food material containing microparticles that are finely crushed and ground by mastication and keep a spherical shape unless they are masticated; a second step of enlarging the artificial food material having been thus masticated by applying pressure to a thickness equal to the diameter of the microparticles while sandwiching the artificial food material between two preparation sheets; and a third step of counting microparticles keeping the spherical shape that remain in the artificial food material having been enlarged between the two preparation sheets by applying pressure. By using this evaluating system in the invention, the masticatory efficiency can be evaluated well in precise and at short time without using a solvent and expensive instruments.

2 Claims, No Drawings

EVALUATING SYSTEM OF MASTICATORY EFFICIENCY AND ARTIFICIAL FOOD MATERIAL

TECHNICAL FIELD

The present invention relates to an evaluating system of a masticatory efficiency and an artificial food material to be used in the evaluating system.

BACKGROUND ART

Human naturally suckle by instinct, however, as teeth appear in the weaning period, they begin training to eat a solid foods little by little thereby learning mastication. Mastication is a series of actions for processing food into a state so as to enable the food to be swallowed (deglutition) as small food materials by cutting and crushing the food involving with almost all organs in the mouth such as teeth, tongue, lips, cheeks and throat. When a learning action of mastication is neglected, dental caries between teeth or a fisher caries of molar tooth, a snaggletooth, or gingivitis is liable to be caused. This mastication is similar to a state in which rice cake is pounded in a mortar. That is, a pestle and a mortar correspond to teeth and what participate in kneading are tongue, lips, and cheeks.

Further, teeth do not attach to the bone of the jaw, but a membrane (periodontal ligament) with a thickness of about 200 µm is interposed between tooth and bone of jaw and functions as a cushion, and also serves as an extremely sensitive sensor to control the masticatory movement. During mastication, a load of several tens kilograms, that is, a force of about half the body weight acts on between the upper and lower teeth. At this time, the periodontal ligament is compressed and reduced to a thickness of less than 100 µm. In this manner, direct collision of the upper and lower teeth is avoided, and sensing is performed so as to prevent the teeth from being damaged by a foreign matter such as sand. This is similar to a phenomenon that a pestle does not directly hit a mortar when rice cake is pounded.

As described above, a masticatory efficiency has very great significance for humans. Therefore, an importance has been placed on objective examination of a masticatory efficiency and accurate evaluation of the examination results as basic objects of the dental health care, and many studies have been made since a long time ago.

However, the fact is that with these study results, the accuracy has not reached such a level that the method can be applied to a stage of clinical dentistry.

On the other hand, a technique for the function of general organ, for example, a visual acuity test in the ophthalmology, and a hearing test in the otolaryngology, has been developed and adopted in the medical department since a long time ago, which has made a huge contribution to advancement from an academic view point and development of therapeutic techniques. However, the fact is that there has been almost no technique for a test of a masticatory efficiency in the dentistry.

In light of the above circumstances, the present inventors have developed and proposed "Sosyaku Kino Hyoka-yo no Kinosei Biryushi wo Ganyu suru Jinko Syokkai (Artificial food material containing functional microparticles for evaluating masticatory efficiency)" characterized by containing a lot of functional microparticles for evaluating a masticatory efficiency which have a substantially uniform spherical shape and are only squashed by an occlusion pressure and are not crushed (Japanese Patent No. 2900947).

A person with malocclusion was allowed to masticate this artificial food material, and a masticatory efficiency could be objectively and accurately evaluated. In this method, after the person is allowed to masticate 100 chewing strokes an artificial food material obtained by containing spherical microparticles which get flattened during mastication without being crushed even if they are masticated in a chewing gum base, only the microparticles are separated by removing the gum base and passed through a sieve with slit-like pores, and then, spherical microparticles and flattened microparticles are tried to be accurately measured using an electron balance.

However, in this evaluation method, problems as described below remained.

Firstly, a method for producing the microparticles to be incorporated in the artificial food material could be applied to a laboratory. However, its technique has not yet fully developed as an industrial production method and it was difficult to produce a large amount of microparticles enough to be used by each dentist.

Secondly, there was a problem that in a process of measuring a ratio of deformed microparticles after masticating, a large amount of an organic solvent such as dichloromethane was required to be used.

Thirdly, in this evaluation method, a relatively expensive equipment was needed, and further, it took a long time of 1 hour or more to perform the measurement.

Due to these reasons, although this technique is a method for evaluating a masticatory efficiency that enables sufficient evaluation using an equipment and the like which a dental research institute usually has, it was difficult to evaluate of a masticatory efficiency in a dental clinic, therefore, this technique did not spread sufficiently.

On the other hand, Ishikawa et al. have proposed chewing gum which changes its color for evaluating a masticatory ability of a person using denture J Jpn Prosthodont Sci., 46, 103-109 (2002)). This is useful for qualitative evaluation, but it is difficult to quantitatively evaluate a masticatory ability by this method.

Accordingly, an object of the invention is to provide a system for evaluating a masticatory efficiency with high accuracy in a short time without using an organic solvent and an expensive equipment for evaluation.

Patent document 1: Japanese Patent No. 2900947
Non-patent document 1: J Jpn Prosthodont Sci., 46, 103-109 (2002)

DISCLOSURE OF THE INVENTION

Problems that the Invention is to Solve

To solve the problems as described above, the present inventor advanced intensive studies of properties of microparticles to be contained in an artificial food material, and found that the above-mentioned three problems could be solved at once by changing the conventional basic way of thinking of "using particles that are only squashed by an occlusion pressure and are not crushed" and instead using "microparticles that are in a substantially uniform spherical shape and have a property of being finely crushed and ground by masticating", and thus the present invention has been completed.

Means for Solving the Problems

That is, the system for evaluating a masticatory efficiency of the invention is characterized by comprising a step of allowing a human subject to masticate an artificial food material containing microparticles that are finely crushed and ground by masticating and have a spherical shape unless they are masticated; a step of enlarging the artificial food material having been thus masticated by applying pressure to a thickness equal to the diameter of the microparticles while sandwiching the artificial food material between two preparation sheets; and a step of counting microparticles retaining the spherical shape that remain in the artificial food material having been enlarged between the two preparation sheets by applying pressure.

Further, the artificial food material of the invention is characterized by containing microparticles that are finely crushed and ground by masticating and have a substantially uniform spherical shape unless they are masticated.

Effect of the Invention

The evaluating system of a masticatory efficiency of the invention is capable of performing measurement with high accuracy in an extremely short time of about 5 minutes or so without using an organic solvent and an expensive equipment for evaluation, therefore, the system is expected to be applied widely in clinical dentistry.

BEST MODE FOR CARRYING OUT THE INVENTION

The first step of the evaluating system of a masticatory efficiency of the invention is a step of allowing a human subject to masticate an artificial food material containing microparticles that are finely crushed and ground by mastication and keep a spherical shape unless they are masticated.

The requirement of "microparticles that are finely crushed and ground by mastication and keep a spherical shape unless they are masticated" to be used in the first step of the invention is that the microparticles are finely crushed and ground by mastication and keep a spherical shape unless they are masticated. It is needless to say that the microparticles are required to be made of a material harmless to the human body because they are put in the mouth. Further, more it is known that during mastication, as a compression force which is an occlusion pressure, a force of about 2.0 kgw/mm² acts on between the upper and lower teeth. Further, it is also known that during mastication, each tooth is displaced by about 100 μm.

As the microparticles that satisfy the above requirement, for example, substantially uniform spherical microparticles prepared using carnauba wax which is a kind of natural wax are preferred, and the diameter of the particles is from about 100 to 500 μm.

A most preferred example of the artificial food material is polyisobutylene, for example, commercially available chewing gum. In the invention, the "microparticles that are finely crushed and ground by mastication and keep a spherical shape unless they are masticated" are mixed and contained in polyisobutylene which is a chewing gum base component thereby attempting to prevent the microparticles from being lost by scattering.

The second step of the evaluating system of a masticatory efficiency of the invention is a step of enlarging the artificial food material having been thus masticated by applying pressure to a thickness equal to the diameter of the microparticles while sandwiching the artificial food material between two preparation sheets.

For easily measuring crushed microparticles in the clinical dentistry, it is necessary that an organic chemical, an expensive instrument, or the like is not used. Therefore, in the second step of the invention, the artificial food material is sandwiched between two preparation sheets, for example, glass plates, plastic plates such as acrylic plates, or plastic films, and enlarged by applying pressure to a thickness equal to the diameter of the microparticles.

The third step of the evaluating system of a masticatory efficiency of the invention is a step of counting microparticles retaining the spherical shape that remain in the artificial food material having been enlarged between the two preparation sheets by applying pressure.

In advance, the containing number of the microparticles having a spherical shape in the artificial food material to be used for evaluating a masticatory efficiency is measured per unit area, the containing number of the microparticles keeping the spherical shape that remain in the artificial food material after being masticated by a human subject are directly counted per unit area and its ratio is calculated, as the result a remaining ratio of the spherical microparticles is obtained, and from the ratio, a crushing ratio of microparticles can be obtained. Since there is a large difference in this value between a healthy person who can perform normal masticating and a person with malocclusion, a condition of mastication of each individual can be evaluated from this value.

In addition, to evaluate a condition of mastication of each individual, in the same manner as a masticatory efficiency being represented by a flattened particle ratio (flattened capsule ratio) described in the above-mentioned Japanese patent No. 2900947 or Kobyo shi (Kokubyo Gakkaizasshi: Journal of the Stomatological Society) 56: 4513-527 (1989), a masticatory ability can be represented by a crushing ratio at single chewing stroke in mastication. That is, when an incidence ratio of crushed particles is taken as an issue of a failure ratio in a probability theory, a probability that a certain microparticle having a spherical shape is crushed by mastication is constant throughout each chewing stroke during mastication, the incidence ratio is in accordance with an exponential distribution. When a ratio of crushed particles in the artificial food material after mastication t times to the entire spherical particles before masticating is defined to be a crushing ratio p(t) of spherical particles, and a ratio of remaining particles in the artificial food material after mastication t times to the entire spherical particles before mastication is defined to be a remaining ratio q(t) of spherical particles, in consideration of the fact that the crushing ratio is in accordance with an exponential distribution, the crushing ratio p(1) at single chewing stroke in mastication is as the following equation (1).

$$p(1)=1-q(1)=1-(1-p(t))^{1/t} \qquad (1)$$

Then, by comparing the value of p(1) of a human subject who has a normal masticatory efficiency to that of a test subject, condition of a mastication (masticatory ability) of the test subject can be universally represented.

In future, when the number of test subjects is large, or data processing is performed in a large area, for example, nationwide, accurate counting can be performed by so-called evolutionary image processing proposed by Professor Tomoharu Nagao (Yokohama National University) (Image Lab, 64-67 (2005, 9)).

Example

Hereinafter, a configuration of the present invention will be specifically described with reference to Example.

[Production of Spherical Microparticles]

Purified carnauba wax manufactured and distributed by Yokozeki Oil & Fat Corp. was finished into spherical microparticles using a surface-modifying machine "Meteo Rainbow" MR-50 manufactured by Nippon Pneumatic MFG Co., Ltd.

These spherical microparticles were passed through a sieve, whereby substantially uniform carnauba spherical microparticles having a diameter of about 250 µm were obtained.

250 g of the thus obtained carnauba spherical microparticles were added to 1700 g of polyisobutylene (trade name "HIMOL 6H") manufactured by Nippon Petrochemicals Co., Ltd., and mixed therein.

The obtained gum was formed into a spherical shape (0.6 g) with a diameter of 11 mm, whereby a gum-like artificial food material for evaluating a masticatory efficiency.

[Test for Number of Chewing Stroke in Mastication]

A basic test was performed for confirming an adequate number of chewing stroke in mastication and reproducibility of measurement values.

A test subject who has a normal masticatory efficiency was allowed to masticate one piece of the above-mentioned artificial food material for evaluating a masticatory efficiency by predetermined number of chewing strokes. After masticating, the sample having been thus masticated was enlarged to a thickness of about 250 µm using two sheets of laminated glass (preparation sheets), and a remaining ratio of spherical microparticles was counted. A crushing ratio of carnauba spherical microparticles at single chewing stroke in mastication and a remaining ratio of spherical particles after measurement were calculated for each predetermined number of chewing stroke in mastication after masticating according to the above-mentioned equation (1). The results are shown in Table 1.

TABLE 1

| Number of chewing strokes in mastication | 20 times | 30 times | 50 times |
|---|---|---|---|
| Crushing ratio at single chewing stroke in mastication (%) | 2.7 | 2.9 | 2.9 |
| Remaining ratio after measurement (%) | 63.6 | 50.0 | 31.8 |

By this test, it is found that even if the number of chewing stroke in mastication is changed to 20, 30, and 50 times, the crushing ratio of carnauba spherical microparticles at single chewing stroke in mastication becomes substantially constant. Accordingly, it was confirmed that as an adequate number of chewing stroke in mastication, 20 to 30 times are preferred, and the reproducibility of measurement values is high.

Example 1

To confirm the level of the performance of evaluating the degree of malocclusion, a masticatory test was performed with respect to a test subject A with mild malocclusion, a test subject B with moderate malocclusion, a test subject C with severe malocclusion, and a test subject D with a normal oral condition with the prior consent.

An artificial food material used for the evaluation of a masticatory efficiency was the same one as used in the above test for number of chewing stroke in mastication.

The masticatory test was performed in the same manner as the above test for number of stroke in mastication except that the number of stroke in mastication was changed to 25 times. However, the test was performed three times for the same test subject. A remaining ratio of the spherical microparticles was measured for each sample, and a crushing ratio of carnauba spherical microparticles at single chewing stroke in mastication was calculated. An average of the ratios is shown in Table 2.

TABLE 2

| Test subject | A | B | C | D |
|---|---|---|---|---|
| Crushing ratio at single chewing number in mastication (%) | 1.8 | 1.5 | 0.6 | 2.9 |

As a result, as compared with the test subject with a normal oral condition, the crushing ratio of carnauba spherical microparticles at single chewing stroke in mastication is smaller in the test subject A with mild malocclusion, the test subject B with moderate malocclusion, and the test subject C with severe malocclusion, and the ratio becomes smaller as the condition of malocclusion becomes worse. In this manner, in comparison with the value of crushing ratio of spherical microparticles at single chewing in mastication of a test subject with a normal oral condition, a masticatory efficiency of a test subject can be evaluated with high accuracy.

INDUSTRIAL APPLICABILITY

The evaluating system of a masticatory efficiency of the invention is capable of measuring a masticatory efficiency in an extremely short time of about 5 minutes or so without using an organic solvent and an expensive equipment for evaluation, therefore, the system is expected to be applied widely in the clinical dentistry.

The invention claimed is:

1. A method for evaluating masticatory efficiency, comprising:
    a first step of allowing a human subject to masticate an artificial food material containing a base component and microparticles, the microparticles being finely crushed and ground by mastication and keeping a spherical shape unless they are masticated, the microparticles being mixed and contained in a predetermined amount in the base component;
    a second step of enlarging the artificial food material having been thus masticated by applying pressure to a thickness equal to the diameter of the microparticles while sandwiching the artificial food material between two preparation sheets; and
    a third step of counting microparticles keeping the spherical shape that remain in the artificial food material having been enlarged between the two preparation sheets by applying pressure.

2. The method for evaluating masticatory efficiency of claim 1, wherein the microparticles are carnauba wax microparticles.

* * * * *